United States Patent [19]

Sugiyama

[11] Patent Number: 4,837,144

[45] Date of Patent: Jun. 6, 1989

[54] METHOD OF MEASURING LIPID-BOUND SIALIC ACID

[75] Inventor: Masami Sugiyama, Tokyo, Japan

[73] Assignee: Fujirebio Kabushiki Kaisha, also trading as Fujirebio Inc., Tokyo, Japan

[21] Appl. No.: 40,482

[22] Filed: Apr. 20, 1987

[30] Foreign Application Priority Data

Apr. 25, 1986 [JP] Japan ................................ 61-94613

[51] Int. Cl.$^4$ .......................... C12Q 1/00; C12Q 1/34; G01N 21/78; G01N 31/02
[52] U.S. Cl. ......................................... 435/4; 435/18; 436/64; 436/71; 436/93; 436/94; 436/164; 436/175; 436/177
[58] Field of Search ...................... 436/64, 71, 86, 87, 436/88, 93, 94, 164, 175, 177, 178; 435/4, 18

[56] References Cited

U.S. PATENT DOCUMENTS

| | | | |
|---|---|---|---|
| 4,115,062 | 9/1978 | Morre et al. | 436/64 |
| 4,342,567 | 8/1982 | Katopodis et al. | 436/164 X |
| 4,457,865 | 7/1984 | Miller | 436/64 X |
| 4,493,898 | 1/1985 | Sallay | 436/64 |
| 4,520,111 | 5/1985 | Miller | 436/71 X |
| 4,701,418 | 10/1987 | Katopodis | 436/93 X |
| 4,748,128 | 5/1988 | Katopodis | 436/178 X |

FOREIGN PATENT DOCUMENTS

| | | | |
|---|---|---|---|
| 0159563 | 10/1985 | European Pat. Off. | 436/71 |
| 0159564 | 10/1985 | European Pat. Off. | 436/71 |
| 60-78597 | 5/1985 | Japan. | |
| 0071856 | 4/1987 | Japan. | |

OTHER PUBLICATIONS

Sugahara et al., Clin. Chim. Acta, vol. 108, pp. 493–498, 1980.
"Improved Method to Determine Lipid Bound Sialic Acid In Plasma or Serum", Katopodis et al., Research Comm. in Chem. Path. & Pharmacology, vol. 30, No. 1, Oct. 1980.
J. Jpn. Soc. Cancer Ther. 18(3): 692–703, Apr., 1983 "Total Sialic Acid and Lipid Bound Sialic Acid in Sera of Digestive Cancer Patients", Oki.
*Laboratory Techniques in Biochemistry & Molecular Biology,* "Techniques of Lipidology", Kates, 1972, Chapter 3, pp. 347–353.

*Primary Examiner*—Robert J. Hill, Jr.
*Attorney, Agent, or Firm*—Burgess, Ryan & Wayne

[57] ABSTRACT

A method of measuring lipid-bound sialic acid (LSA) which comprises, mixing a LSA separating agent comprising a polar solvent with a sample containing LSA and other sialic acid(s), separating the precipitate formed to obtain a supernatant, and measuring the sialic acid concentration of said supernatant by using an enzyme capable of acting on sialic acid in a lipid-bound state. When a sample is treated with the LSA separating agent comprising a polar solvent, various components in the sample such as protein-bound sialic acid and proteinous substances precipitate while the desired lipid-bound sialic acid remains in the supernatent. Accordingly, by measuring sialic acid concentration of the supernatant, LSA concentration of the sample is easily determined. The method of the invention is simple and superior in reproducibility. The method of the invention is suitable for treating a large number of samples, and it can easily by automated. This method is suitable as a screening test for cancer.

6 Claims, No Drawings

METHOD OF MEASURING LIPID-BOUND SIALIC ACID

BACKGROUND OF THE INVENTION

1. Field of the Invention

This invention relates to a method of measuring lipid-bound sialic acid (LSA) and a LSA separating agent for the same.

2. Description of the Prior Art

Recently, it has been reported that when persons suffer from cancer, LSA concentration in their blood increases. Regarding this increase in LSA concentration, many reports have been made. It has also been reported that even in a patient having primary gastric cancer whose total sialic acid concentration has not increased yet, LSA concentration of the patient has significantly increased (Oki, S., J. Jpn. Soc. Cancer Ther., vol 18, pp 692–703 (1983)).

As method of measuring LSA, the method developed by N. Katopodis et al. (Res. Commun. Clin. Path. Pharm., vol. 30, pp 171–180 (1980)) has widely been employed. This method comprises the following steps. First, each serum is pipetted into a test tube and distilled water is added. The mixture is cooled to 4° C. and an extractant (chloroform : methanol=2:1) is added. This mixture is vigorously stirred for 30 seconds and centrifuged at room temperature. The supernatant is put into another test tube and an aqueous phosphotungstic acid solution is added to precipitate LSA. The precipitate is collected by centrifuging and dissolved in distilled water. A resorcinol reagent is added to the solution and allowed to react at 100° C. for 20 minutes. After being cooled to room temperature, a solvent mixture of butyl acetate-butanol is added to extract a colored material. Absorbance of the butyl acetate-butanol layer is measured to determine LSA concentration of the sample.

Since the method of Katopodis et al. is complicated as mentioned above, an enzyme method has been developed (Japanese Patent KOKAI No. 60-78597). In this method, after pretreatments of a sample, such as dilution and solvent extraction of free fatty acids etc., the sample is divided into two parts. One part is kept for measuring total sialic acid, and phosphotungstic acid is added to the other part to precipitate LSA. The sialic acid concentration of the part not treated with phosphotungstic acid and the supernatant of the other part treated with phosphotungstic acid are measured by the enzyme method such as developed by Sugahara et al. (Clin. Chim. Acta, vol. 108, pp 493–493 (1980)) where neuraminidase and N-acetylneuraminic acid aldolase are employed. LSA concentration of the sample is determined by subtraction of the above two sialic acid concentrations. This method is simpler than the previous method, but in this method, LSA concentration is indirectly determined by subtraction.

SUMMARY OF THE INVENTION

An object of the invention is to provide a method of measuring LSA which is simple to operate.

Another object of the invention is to provide a method of measuring LSA wherein the measured values are exact and highly reliable.

Another object of the invention is to provide a method of measuring LSA which is superior in reproducibility.

Still another object of the invention is to provide a LSA separating agent which is superior in separation of other sialic acid such as protein-bound sialic acid from LSA and suitable for the method of measuring LSA using the foregoing enzyme method.

In order to achieve such objects, the present inventor has investigated, and he has completed the present invention. The present invention is based upon the following two discoveries. First, when sample containing various states of sialic acid are treated with a LSA separating agent comprising a polar solvent, the sialic acids other than LSA precipitate while LSA remains in the supernatant. That is, LSA can easily be separated without complicated operations. Second, LSA in the supernatant can be determined by the enzyme method developed by Sugahara et al. without special operation, and the results are consistent with the conventional method of Katopodis et al.

Thus, the present invention relates to a method of measuring LSA which comprises mixing a LSA separating agent comprising a polar solvent with a sample containing various states of sialic acid in addition to LSA, separating the precipitate formed to obtain a supernatant, and measuring the sialic acid concentration of the supernatant by using an enzyme capable of acting on sialic acid in a lipid-bound state, and relates to a LSA separating agent comprising a polar solvent for the above method.

DETAILED DESCRIPTION OF THE INVENTION

The LSA separating agent comprises a polar solvent. Suitable polar solvents include methanol, ethanol, propanol, isopropanol, dimethylformamide and acetonitrile. Two or more polar solvents may be used. The LSA separating agent may be composed of a polar solvent alone, or it may contain another component. For example, a small amount of water or an aqueous solution of a protein precipitant such as heparin may be added to a polar solvent. In this case, suitable content of the polar solvent is more than 90 vol.%.

The amount of the LSA separating agent to be added is determined mainly based upon the protein content of each sample. In the case where the sample is serum, suitable amount of the 28a separating agent is 1.2 to 1.6 time by volume the amount of serum. The reaction time of the LSA separating agent may be 5 to 30 seconds at room temperature. The precipitate formed is separated by filtration or centrifuging. Filtration using a tube filter is preferable for automation.

Sialic acid concentration of the supernatant is measured by using an enzyme capable of acting on sialic acid in a lipid-bound state. Such an enzyme includes neuraminidase. In this method, sialic acid existing in a lipid-bound state is liberated by neuraminidase to produce N-acetylneuraminic acid which is a free sialic acid, and N-acetylneuraminic acid is decomposed by N-acetylneuraminic acid aldolase to N-acetylmannosamine and pyruvic acid. Then, the amount of the pyruvic acid may be determined by a known method. For example, the pyruvic acid is oxidized by pyruvate oxidase to produce $H_2O_2$, and $H_2O_2$ is allowed to react with 4-aminoantipyrine and an oxidative condensing agent such as p-chlorophenol or N-ethyl-N-($\beta$-hydroxyethyl)-m-toluidine in the presence of peroxidase to produce red violet color. Then, this color is determined by measuring absorbance at 550 nm. LSA concentration can be calculated from the result. The reagent kit for this enzyme method is commercially available. Besides, lactate dehydrogenase is allowed to react with the above pyruvic acid in the presence of NADH as a coenzyme, and decrease of the NADH may be determined by measuring absorbance at 340-370 nm. LSA concentration can also be calculated from the result.

When a sample is treated with a LSA separating agent comprising a polar solvent, various components in the sample such as protein-bound sialic acid and proteinous substances precipitate while the object lipid-bound sialic acid remains in the supernatant. Accordingly, by measuring sialic acid concentration of the supernatant, LSA concentration of the sample is easily determined. The method of the invention is simple and superior in reproducibility. The method of the invention is suitable for treating a large number of samples, and it can easily be automated. This method is suitable as a screening test for cancer.

EXAMPLES

Example 1

95 parts of a solvent mixture of methanol/dimethylformamide (1/1 v/v) was mixed with 5 parts of distilled water, and used as a LSA separating agent. 150 μl of this LSA separating agent was added to 100 μl of sample serum, and vigorously stirred by a mixer for 10 seconds. Precipitate formed was separated by a centrifuge at 3,000 rpm (more than 1,000 G) to obtain 150 μl of supernatant.

Each 150 μl of the supernatant separated from a sample serum and a standard serum were placed into separate small test tubes, and each 1 ml of the enzyme coloring solution of the reagent kit for measuring sialic acid ("SIALIZYME-550", Fujirebio Inc.) was added to each test tube. This enzyme coloring solution contained neuraminidase, N-acetylneuraminic acid aldolase, 4-aminoantipyrine, pyruvate oxidase, peroxidase, N-ethyl-N-(β-hydroxyethyl)-m-toluidine, $MgCl_2$, FAD, TPP and others. This mixture was allowed to react at 37° C. for 20 minutes, and 2 ml of a reaction terminator solution which was also a member of the above reagent kit was added. Then, absorbance of the mixture at 550 nm was measured. At that time, 150 μl of distilled water was employed instead of the sample serum, and this was used as a reagent blank.

LSA concentration of the sample was calculated by the following formula.

$$\text{LSA (mg/dl)} = \frac{\text{Absorbance of Sample}}{\text{Absorbance of Standard}} \times \text{Sialic Acid}$$

Concentration of Standard × Dilution Times of Sample when 100 μl of a sample is mixed with 150 μl of a LSA separating agent, wherein the above dilution times is 2.5.

In order to examining reproducibility, the above measurement was repeated each 10 times as to two sample sera. The results are shown below.

| n = 0 | Sample A | Sample B |
|---|---|---|
| $X_{max}$ | 13.4 mg/dl | 21.9 mg/dl |
| $X_{min}$ | 12.6 mg/dl | 20.9 mg/dl |
| $\bar{x}$ | 13.2 mg/dl | 21.3 mg/dl |
| SD | 0.32 | 0.34 |
| CV | 2.4% | 1.6% |

CV: Coefficient of Variation

For 26 sample sera, a correlation was made between the result obtained by the above measurement and the result obtained by the conventional Katopodis method. The results are shown below.

n=26
Correlation coefficient r=0.95
Regression formula Y=1.0X−0.5 (mg/dl)
Y: The Present Method
X: Conventional Method Example 2

A mixture of 97 parts of methanol and 3 parts of distilled water was used as the LSA separating agent, and LSA concentrations of the same samples (Sample A and Sample B) were measured in the same manner as Example 1. Measurement was repeated each 10 times, and the results are shown below.

| n = 10 | Sample A | Sample B |
|---|---|---|
| $X_{max}$ | 13.6 mg/dl | 22.4 mg/dl |
| $X_{min}$ | 13.1 mg/dl | 21.1 mg/dl |
| $\bar{x}$ | 13.4 mg/dl | 21.7 mg/dl |
| SD | 0.20 | 0.53 |
| CV | 1.5% | 2.4% |

Correlation to Conventional Katopodis Method n=26
Correlation coefficient r=0.96
Regression formula Y=1.01X+0.7 (mg/dl)

Example 3

A mixture of 95 parts of dimethylformamide/isopropanol (60/40) and 5 parts of distilled water was used as the LSA separating agent and LSA concentrations of the same samples were measured in the same manner as Example 1. The measurement was repeated 10 times, and the results are shown below.

| n = 10 | Sample A | Sample B |
|---|---|---|
| $X_{max}$ | 13.9 mg/dl | 21.8 mg/dl |
| $X_{min}$ | 12.7 mg/dl | 20.4 mg/dl |
| $\bar{x}$ | 13.5 mg/dl | 21.4 mg/dl |
| SD | 0.50 | 0.67 |
| CV | 3.7% | 3.1% |

Correlation to Conventional Katopodis Method n=26
Correlation coefficient r=0.96
Regression formula Y=0.97X+0.9 (mg/dl)

Example 4

As to the same sample serum, measurement of LSA concentration was repeated by the present method and the conventional Katopodis method, and reproducibility of the measured value was compared to each other. The results are shown below.

| n = 10 | The Present Method | Conventional Method |
|---|---|---|
| $X_{max}$ | 12.0 mg/dl | 11.5 mg/dl |
| $X_{min}$ | 10.9 mg/dl | 8.6 mg/dl |
| $\bar{x}$ | 11.7 mg/dl | 10.6 mg/dl |
| SD | 0.41 | 0.90 |
| CV | 3.5% | 8.5% |

I claim:

1. A method of measuring lipid-bound sialic acid in a sample containing lipid-bound sialic acid and other sialic acid(s) which comprises contacting a predetermined amount of a lipid-bound sialic acid separating agent comprising a polar solvent selected from the group consisting of methanol, ethanol, propanol, isopropanol, dimethylformamide, acetonitrile and mixtures thereof, with a predetermined amount of a sample containing lipid-bound sialic acid and other sialic acid(s) to form a precipitate and a supernatant, separating the supernatant from the precipitate formed, and, without further treatment of the supernatent, measuring lipid-bound sialic acid in the sample by measuring the sialic acid concentration in the supernatant using neuraminidase and N-acetylneuraminic acid aldolase.

2. The method of claim 1 wherein said separating agent is a mixture of said polar solvent and water and the concentration of said polar solvent in said separating agent is more than 90 vol.%.

3. The method of claim 1 wherein said separating agent contains a protein precipitant.

4. The method of claim 3 wherein said protein precipitant is heparin.

5. The method of claim 1 wherein said sample is serum and the predetermined amount of said separating agent is 1.2 to 1.6 times by volume the predetermined amount of said serum.

6. The method of claim 1 wherein said polar solvent is a mixture of at least two solvents selected from the group consisting of methanol, ethanol, propanol, isopropanol, dimethylformamide, and acetonitrile.

* * * * *